United States Patent [19]
Kelln et al.

[11] Patent Number: 5,334,349
[45] Date of Patent: Aug. 2, 1994

[54] LIQUID TRANSFER MODULE FOR A CHEMICAL ANALYZER

[75] Inventors: Norman Kelln; Kelsey Loughlin, both of Spokane, Wash.

[73] Assignee: Schiapparelli Biosystems, Inc., Fairfield, N.J.

[21] Appl. No.: 916,208

[22] Filed: Jul. 16, 1992

[51] Int. Cl.⁵ .................................. G01N 21/00
[52] U.S. Cl. ................................. 422/63; 422/100; 436/43; 73/864.24; 73/864.25
[58] Field of Search ............... 422/58, 63, 64, 65, 422/102, 67, 82.05, 82.09, 104, 100; 436/45, 48, 165; 356/246; 73/864.24, 864.25; 74/816, 817

[56] References Cited

U.S. PATENT DOCUMENTS

| | | | |
|---|---|---|---|
| 3,883,305 | 5/1975 | Hoskins et al. | 422/65 |
| 4,234,538 | 11/1980 | Ginsberg et al. | 422/64 |
| 4,313,735 | 2/1982 | Yamashita et al. | 23/230 R |
| 4,699,767 | 10/1987 | Aihara | 422/65 |
| 4,761,268 | 8/1988 | Anderson et al. | 422/72 |
| 4,824,641 | 4/1989 | Williams | 422/100 |
| 4,844,869 | 7/1989 | Rokugawa | 422/64 |
| 5,055,263 | 10/1991 | Meltzer | 422/65 |
| 5,084,242 | 1/1992 | Sakuma et al. | 422/100 |
| 5,085,832 | 2/1992 | Shaw et al. | 422/63 |
| 5,089,229 | 2/1992 | Heidt et al. | 422/64 |
| 5,132,088 | 7/1992 | Wakatake | 122/63 |
| 5,164,318 | 11/1992 | Sato et al. | 435/288 |

FOREIGN PATENT DOCUMENTS

8800704  1/1988  World Int. Prop. O. .

*Primary Examiner*—Nina Bhat
*Attorney, Agent, or Firm*—Wells, St. John, Roberts, Gregory & Matkin

[57] ABSTRACT

A liquid transfer module for a chemical analyzer is adequate to effect liquid transfers between multiple stations arranged in a common arc about a vertical axis on a supporting instrument framework. A rigid radial probe arm supporting a vertical pipette is fixed to a tubular shaft supported on the framework for both rotational and elevational motion relative to the vertical axis. It is surrounded by a powered pulley that imparts angular movement to the shaft. It is elevationally carried by a non-rotating bearing assembly arranged coaxially about the axis on a nut threadably engaged by a powered lead screw extending within the confines of the shaft. Both the elevational and angular positions of the shaft are electronically monitored.

5 Claims, 10 Drawing Sheets

FIG 14

LIQUID TRANSFER MODULE FOR A CHEMICAL ANALYZER

TABLE OF CONTENTS

System Overview
Liquid Transfer Module

TECHNICAL FIELD

This disclosure pertains to a liquid transfer module for a clinical chemistry analyzer for testing of patient samples, such as blood or urine. It generally relates to automatic chemical analyzers for directly measuring properties of reacted liquids, thus producing qualitative and quantitative analyses of tested samples.

BACKGROUND OF THE INVENTION

Automated analyzers have been developed for biochemical analysis of patient samples, such as whole blood, serum, urine, plasma and cerebral spinal fluid. Most such equipment available today is complicated to operate, large in size and high in cost.

The operation of such equipment is technically complicated. It typically requires specialized operators to be available at all times, with commensurate personnel expenses being encountered. It is usually designed for use by large laboratories serving a wide geographic area or by a large medical facility. These existing analyzers carry out tests in a defined sequence of operations designed for efficient, high volume usage.

Such large scale capacity is not always required, particularly in smaller medical clinics where large volumes of blood samples are not encountered on a daily basis. The present chemical analyzer was developed to meet the practical needs of smaller medical settings. It is designed as a desk-top unit that can be operated without specialized laboratory training. Its throughput is adequate for meeting typical clinical applications. As an example, it can be designed to produce a maximum of 164 test results per hour for routine, single reagent chemistries. To provide a representative wide number of reagents, the analyzer has been designed to have a capacity of 40 reagent containers of two different sizes on board. Its capacity can be effectively doubled by utilizing two of the chemistry instruments in tandem, both being controlled by a common workstation.

The compact nature of the analyzer can be partially attributed to the fact that a single probe arm and pipette service all of the functional liquid-handling components included within it. The common pipette is used for transferring samples and reagents, as well as for diluting liquids as needed by particular test requirements. The pipette can be elevationally and angularly positioned with extreme accuracy by use of the present compact operator assembly.

Further details concerning the system will be evident from the following description.

BRIEF DESCRIPTION OF THE DRAWINGS

The preferred embodiment of the invention is illustrated in the accompanying drawings, in which.

DETAILED DESCRIPTION OF THE PREFERRED EMBODIMENT

This disclosure of the invention is submitted in furtherance of the constitutional purposes of the U.S. Patent Laws "to promote the progress of science and useful arts" (Article 1, Section 8).

System Overview

The automatic chemical analyzer (generally illustrated in FIGS. 1-3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

Figure 1:
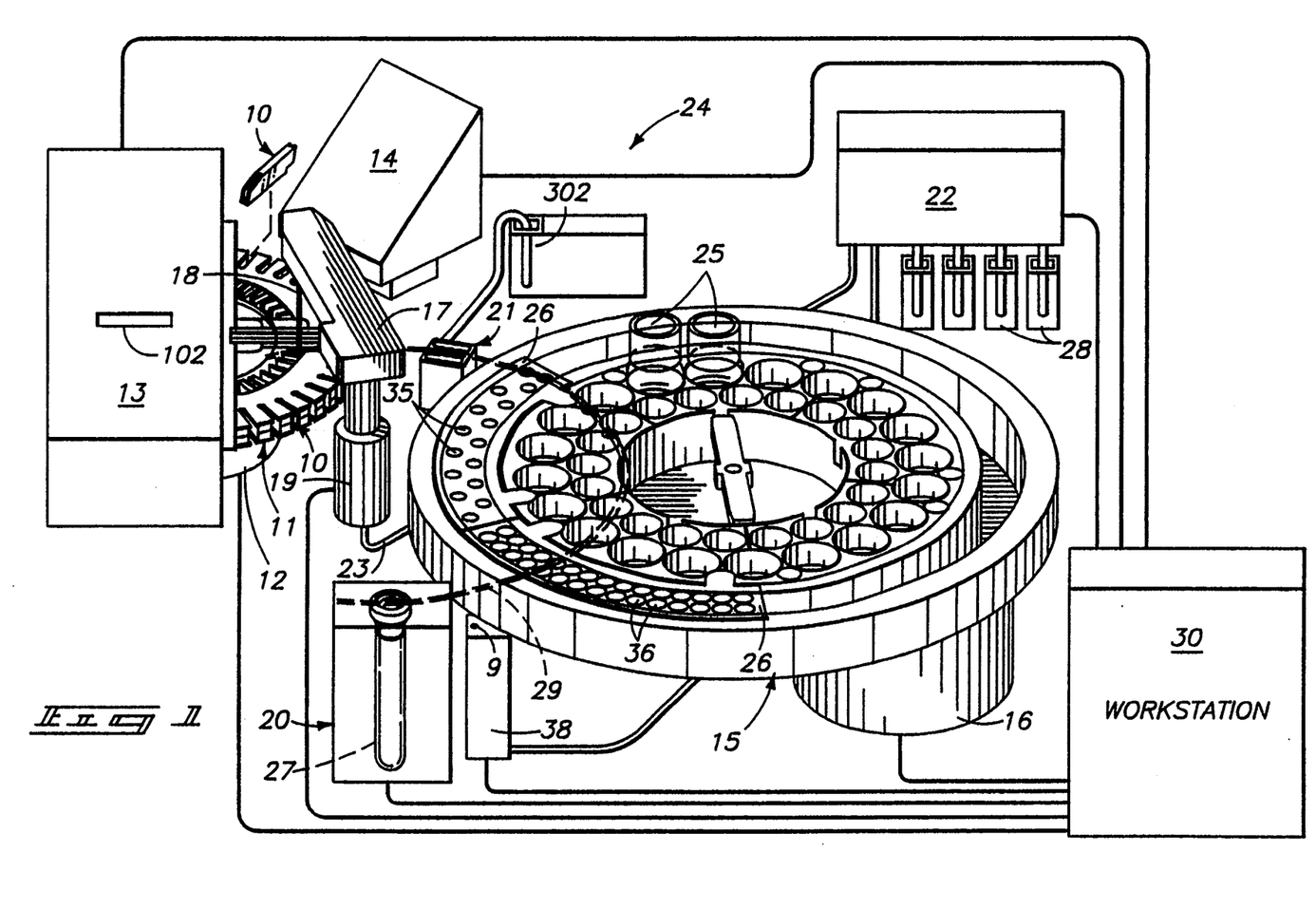
FIG. 1 is a diagrammatic perspective view of the principal components in the analyzer.
Figure 2:
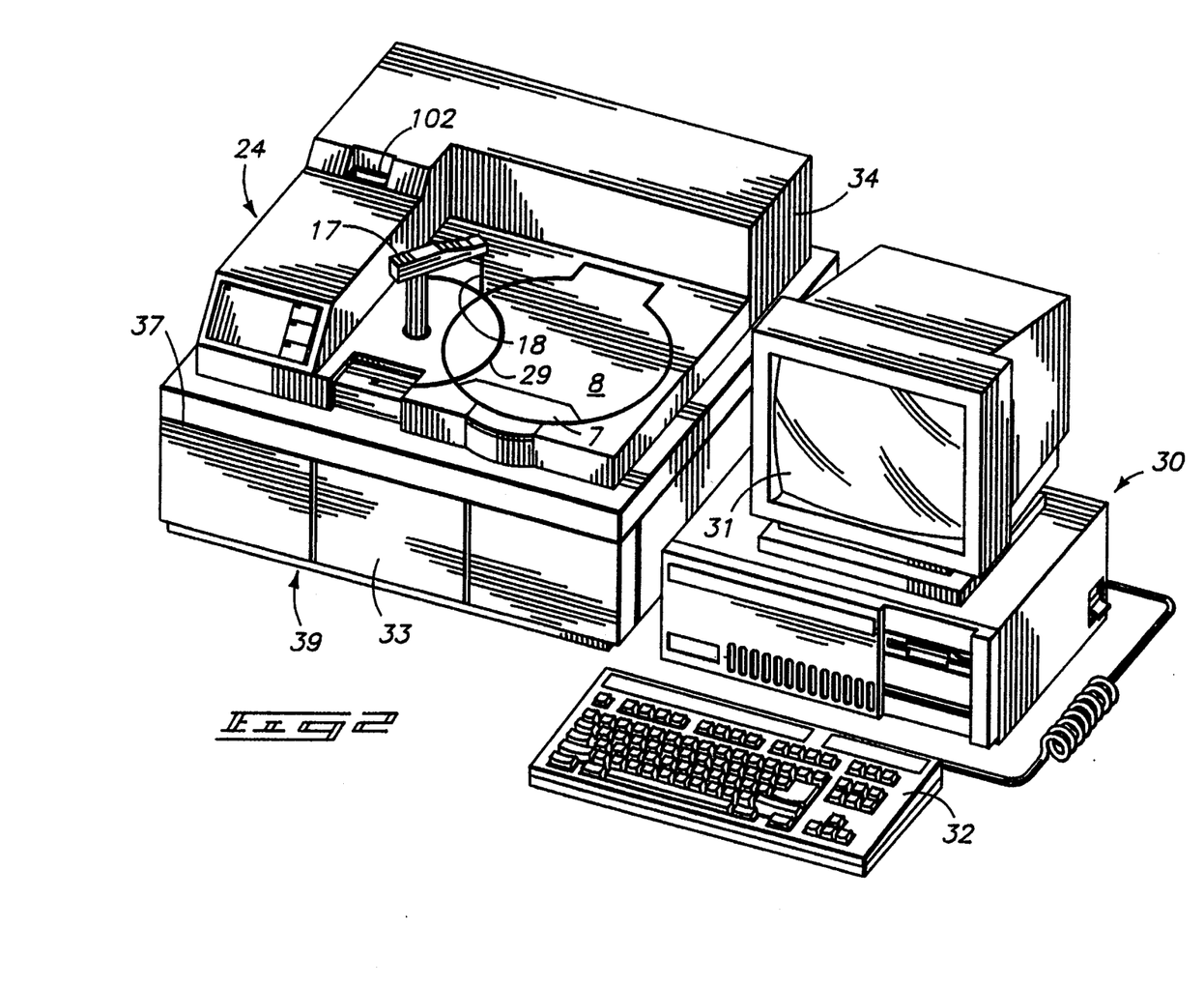
FIG. 2 is a perspective view of the analyzer.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the first axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2–5). It separates along a peripheral parting line 37 defining a lower supporting base 33 and an upper hinged cover 34.

The principal modular components of the chemistry instrument 24 are diagrammatically illustrated in FIG. 1. The illustrated components are specifically designed for use in association with a specially designed liquid cuvette 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors—one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2, 3) formed about the cover 34 of the instrument enclosure. Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidentally impaling adjacent personnel when pipette 18 is subsequently lowered.

A cuvette dispenser module 13 is arranged on the framework of the equipment in a position immediately above the turntable 11. It includes a storage magazine for a plurality of stacks of cuvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown) as new cuvettes are delivered to the turntable 11 by operation of a reciprocating ram. The cuvette disposal container can be a bag or bin into which used cuvettes drop when ejected from turntable 11.

The optical system 14 is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 is rotatably mounted about a vertical axis parallel to and spaced from the axis of turntable 11. It is rotatably powered by a stepper motor 16. Tray 15 consists of a circular reagent bottle support surrounded by separate interlocking ring segments 26.

The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

Figure 3:
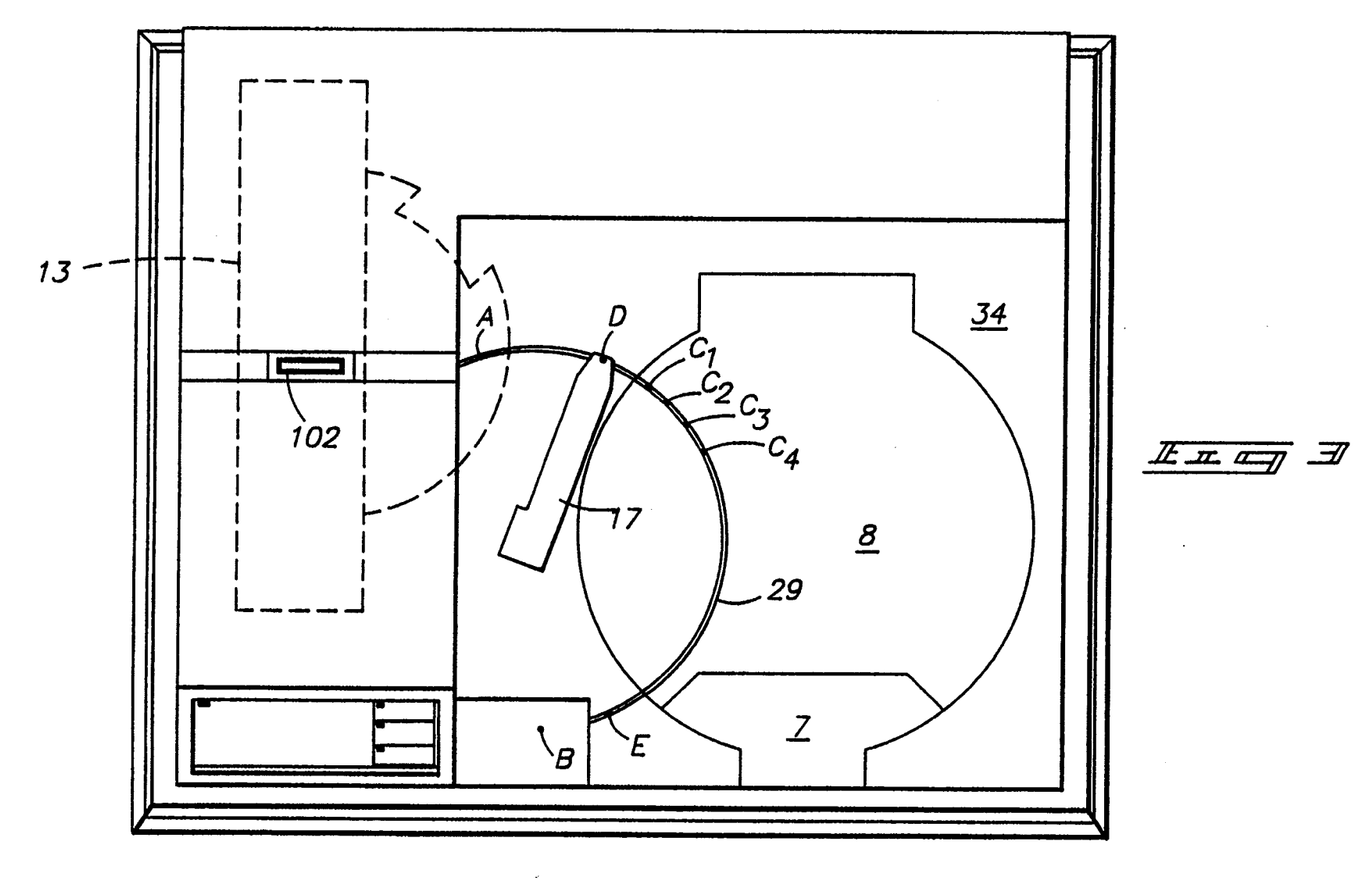
FIG. 3 is a plan view of the chemical instrument enclosure.
Figure 4:
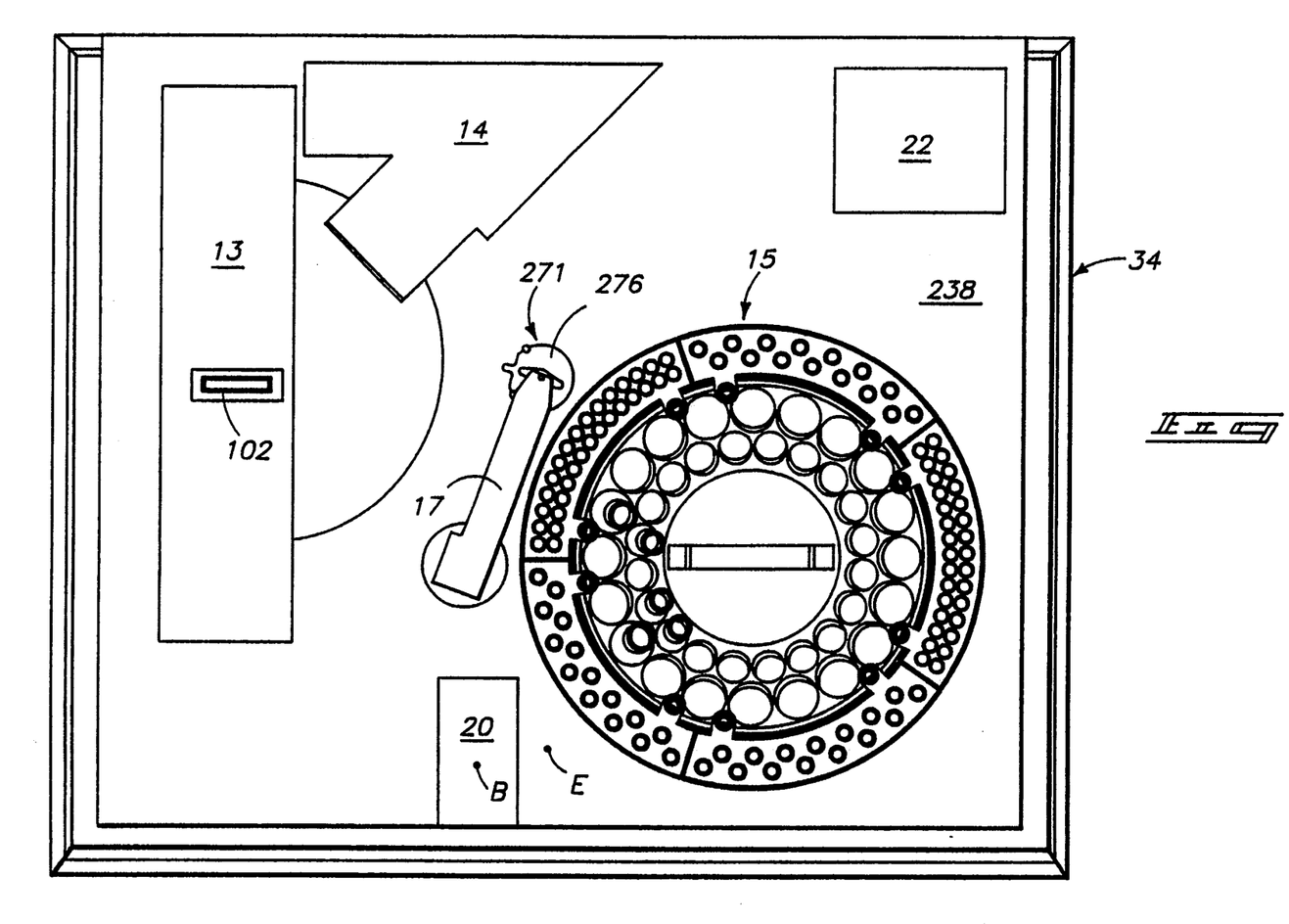
FIG. 4 is a plan view of the chemical instrument enclosure with the cover removed.
Figure 5:
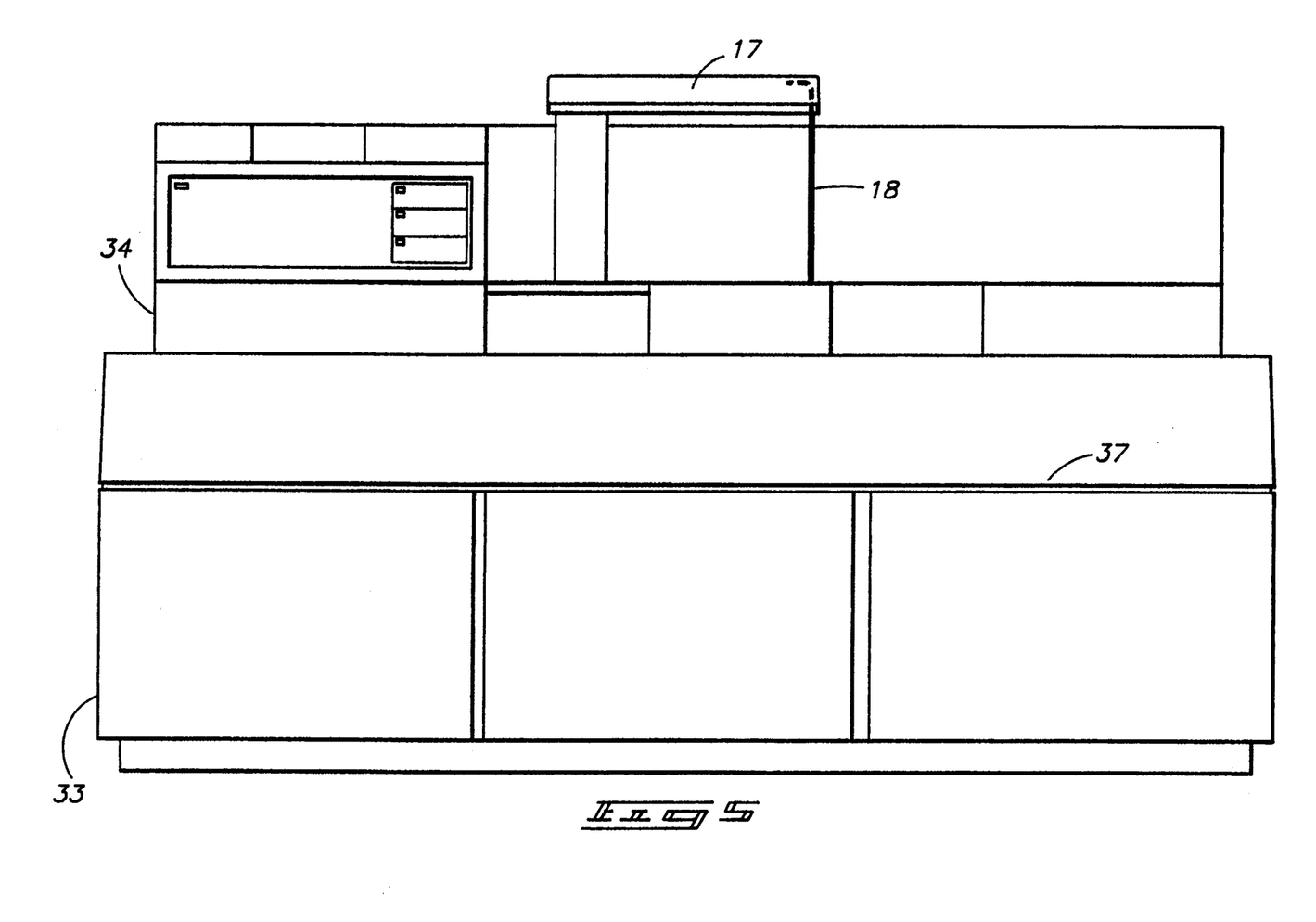
FIG. 5 is a front elevation view of the enclosure.
Figure 6:
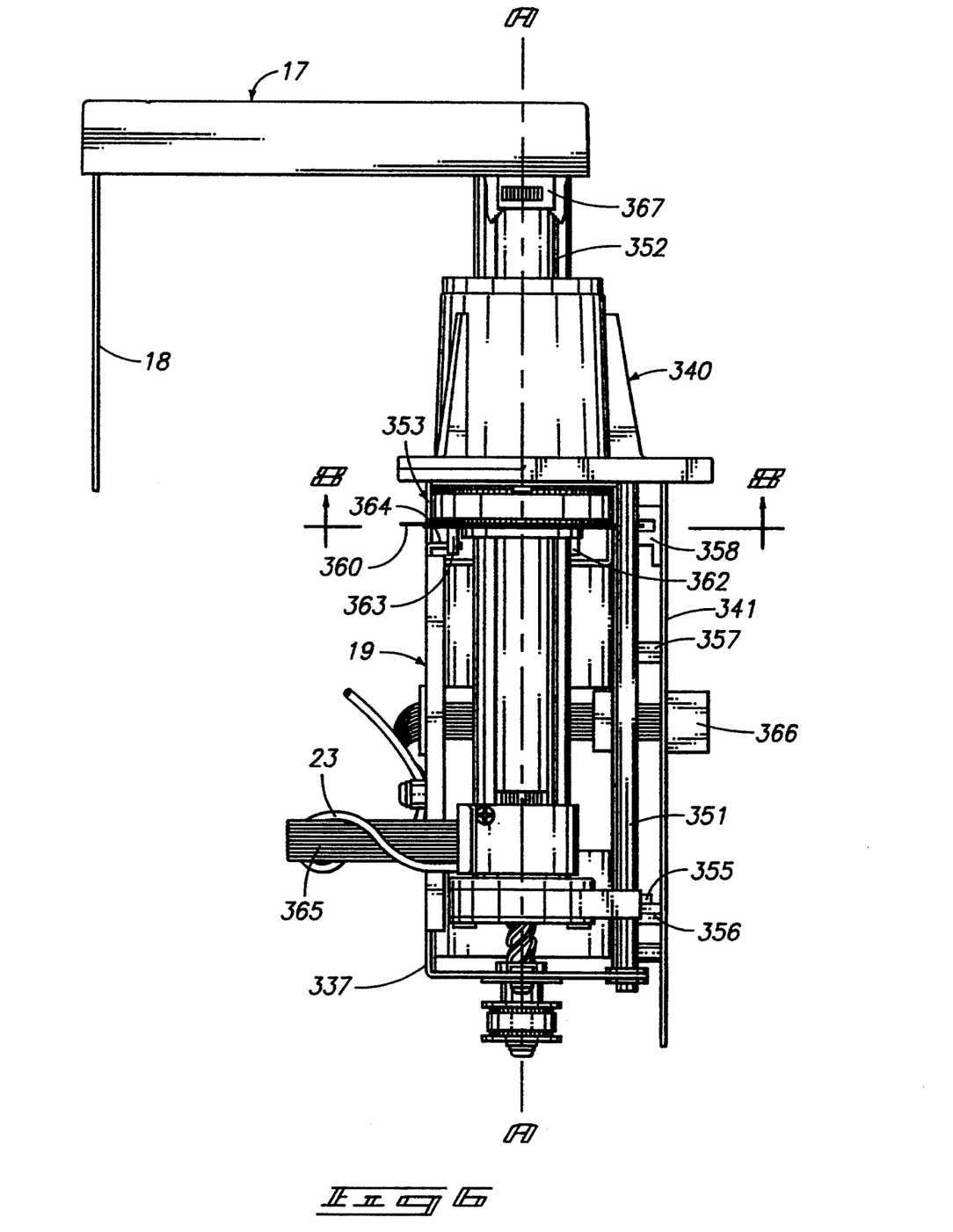
FIG. 6 is a front elevation view of the liquid transfer module.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the areas of the sample/reagent tray 15 and the turntable 11. Heat can be removed from the system by air exchange through a plurality of heat sinks.

A sample tube entry port 20 is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27. The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit is operably connected to the pipette 18 and to conductive members located next to the tray 15 and within the sample tube entry port 20. The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module is of conventional design.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access station $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Liquid Transfer Module

The liquid transfer module which moves preselected volumes of sample liquids, diluents and reagents between the components of the chemistry instrument 24 is designed about the rigid radial probe arm 17 that supports the vertical pipette 18. As schematically shown in FIG. 1, probe arm 17 is supported and powered by operator 19 for moving it angularly and axially relative to a vertical support axis on the framework of the chemistry instrument 24. Suitable sensors are included within the liquid transfer module for detecting the angular and axial position of probe arm 17 relative to the supporting instrument framework.

In general terms, the liquid transfer module is developed about a tubular shaft 352 fixed to and extending beneath the inner end of the probe arm. The tubular shaft 352 is centered about a fixed vertical axis on which the plurality of liquid stations on the framework are arcuately centered. Main bearing means (Shown as bearing assembly 340) operably supports the shaft on the framework for both elevational and pivotal motion of the shaft relative to the framework. A first coaxial drive means (shown as lead screw 345) is operably connected to the shaft for moving it elevationally relative to the instrument framework. A second coaxial drive means (shown as pulley assembly 353) is operably connected to the shaft for moving it angularly relative to the framework.

Details illustrating the structure of the liquid transfer module are shown in FIGS. 6–9. The probe arm 17 is further illustrated in FIGS. 10–14.

The liquid transfer module is structurally supported on cover 34 of the supporting instrument framework by an upright bearing assembly 340. The bearing assembly 340 includes a stationary module frame 337 suspended beneath cover 34. The frame 337 mounts the operator 19 generally described in functional terms in the overview of the system components. It also mounts a printed circuitboard 341 for the electronic and electrical components associated with the liquid transfer module.

The module frame 337 mounts two independently controlled stepper motors 342 and 343. The lower stepper motor 342 (FIG. 7) selectively positions the probe arm 17 in a vertical direction along its support axis (shown at line A—A in FIGS. 6 and 7). The upper stepper motor 343 selectively positions probe arm 17 in an arc about axis A—A.

The module frame 337 also supports a stationary lower bearing assembly 344 that rotatably carries the bottom end of a threaded vertical lead screw 345. Lead screw 345 is coaxially centered about the axis A—A. It can be selectively rotated by stepper motor 342 through an attached lower pulley assembly 346 and an interconnecting flexible timing belt 347.

The vertical tubular shaft 352 coaxially surrounds the lead screw 345. The inner end of probe arm 17 is fixedly attached to the upper end of tubular shaft 352 for movement relative to the instrument enclosure as previously described. An elongated sleeve bearing 355 and upper and lower rotational bearings 338 within bearing assembly 340 suspend the tubular shaft 352 on the instrument framework for both axial and rotational movement relative to the axis A—A.

A cable 365 leads through an axial recess formed along the length of shaft 352 from a connector 366 on printed circuit board 341 to a connector 367 at the underside of probe arm 17. A flexible tube 23 also extends within an axial recess along the exterior of tubular shaft 352 between the lower end of the shaft and a releasable fluid coupling to a fluid conduit within probe arm 17. Tube 23 leads outwardly from the lower end of tubular shaft 352 to the syringe module 22 of the chemistry instrument 24 to control supply of fluids to and from the tip of pipette 18.

The periphery of lead screw 345 is threadably engaged by an encircling nut 348 having interior threads (not shown) that complement and engage the exterior threads along the length of lead screw 345.

The lower end of nut 348 is fixed to a radial guide 350. The radial guide 350 includes axial bearings 333 that rotatably carry the lower end of the tubular shaft 352. Guide 350 encircles and is slidably engaged along a vertical post 351 fixed to the module frame 337. The sliding vertical interconnection between guide 350 and post 351 prevents rotation of nut 348 about the vertical axis of lead screw 345. Rotation of lead screw 345 selectively imparts vertical movement to the non-rotating nut 348 and to the tubular shaft 352 elevationally supported on bearings 333. Because the lower end of tubular shaft 352 an freely rotate relative to the radial guide 350, vertical movement imparted to shaft 352 by operation of stepper motor 342 is independent of the angular position of the shaft about axis A—A.

The outer surface of shaft 352 is slidably guided within a surrounding upper pulley assembly 353 rotatably supported at the lower end of sleeve bearing 355. Shaft 352 is free to move vertically within the surrounding pulley assembly 353, but cannot pivot or rotate relative to it. An interconnection between the pulley assembly 353 and shaft 352 is provided by a radial key 349 projecting radially inward within a full length axial slot or keyway at the exterior of shaft 352.

Pulley assembly 353 is drivingly connected to the output of stepper motor 343 by a second timing belt 354. Operation of stepper motor 343 results in angular motion being imparted to the shaft 352 about vertical axis A—A. The angular movement imparted to shaft 352 by operation of stepper motor 343 is independent of the shaft elevation.

Figure 7:
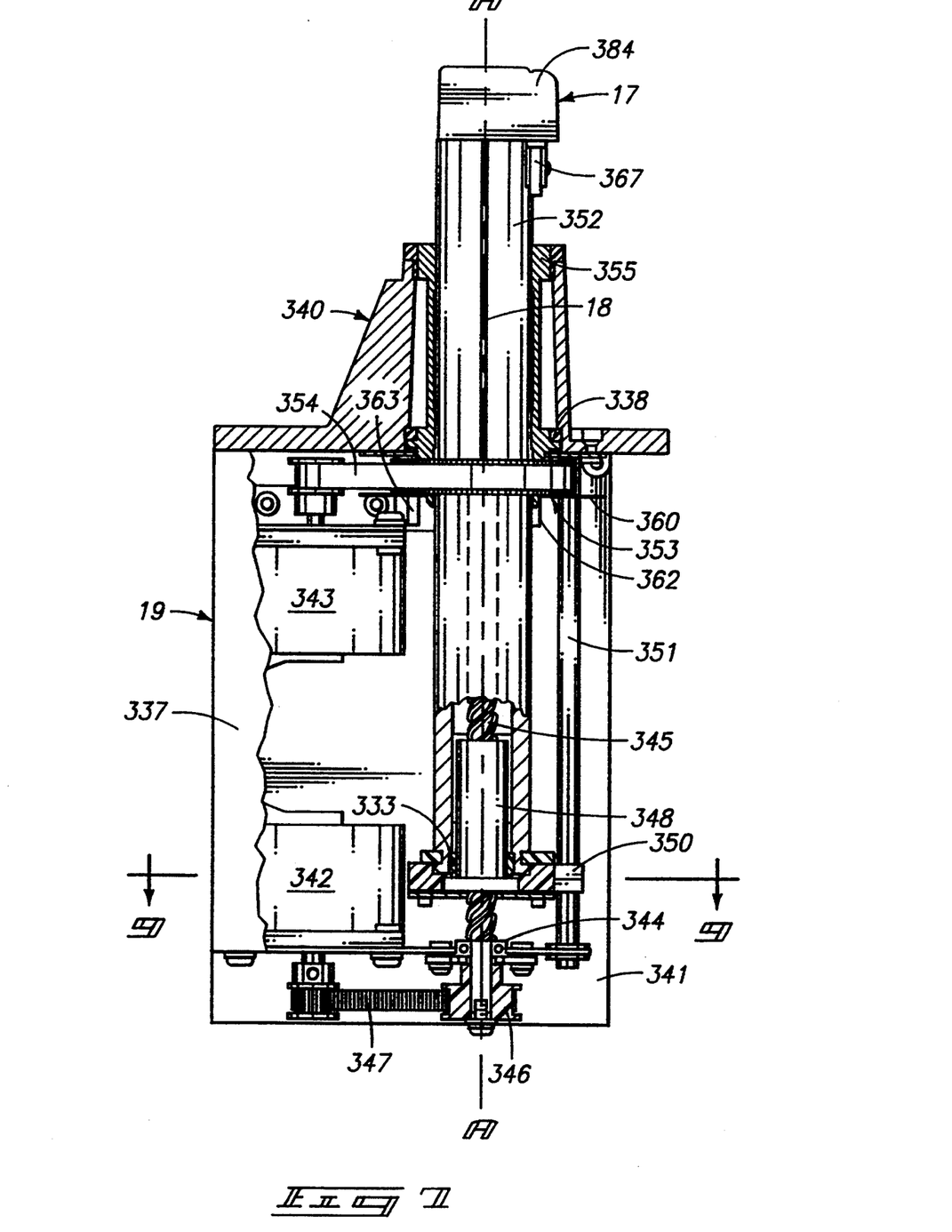
FIG. 7 is a side elevation view, with portions of the module frame being broken away.
Figure 8:
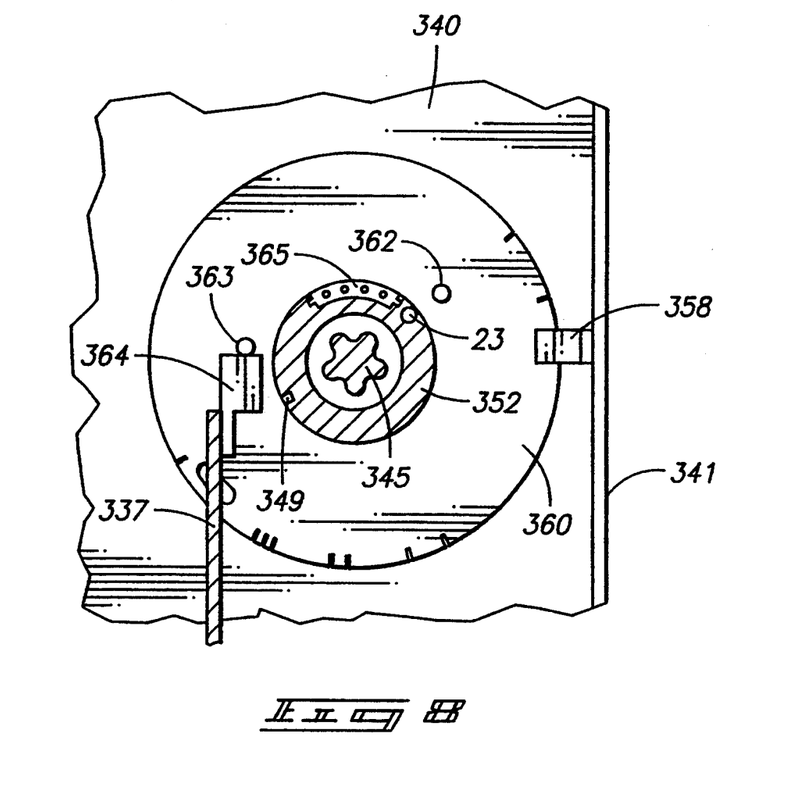
FIG. 8 is an enlarged cross-sectional view taken along line 8—8 in FIG. 6.
Figure 9:
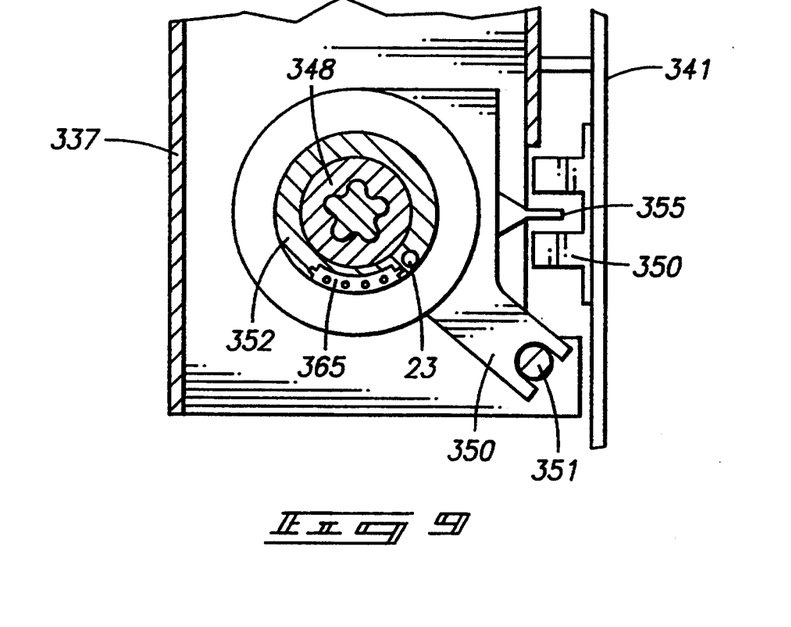
FIG. 9 is an enlarged cross-sectional view taken along line 9—9 in FIG. 7.
Figure 10:
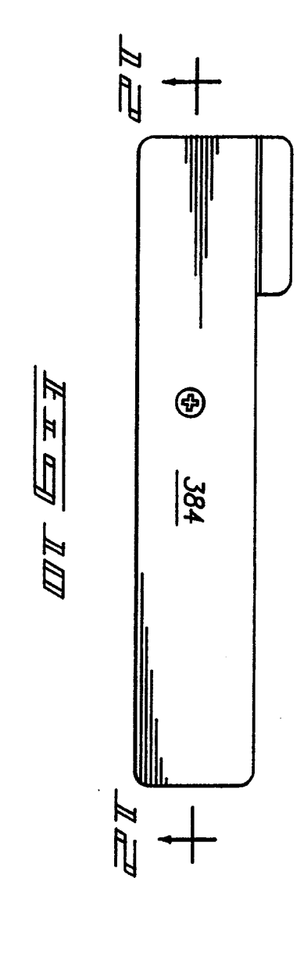
FIG. 10 is a top view of the probe arm.
Figure 11:
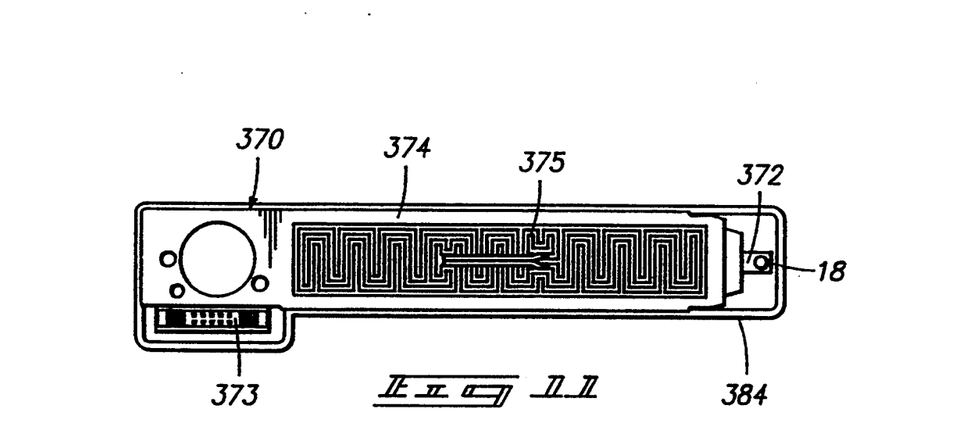
FIG. 11 is a bottom view.
Figure 12:
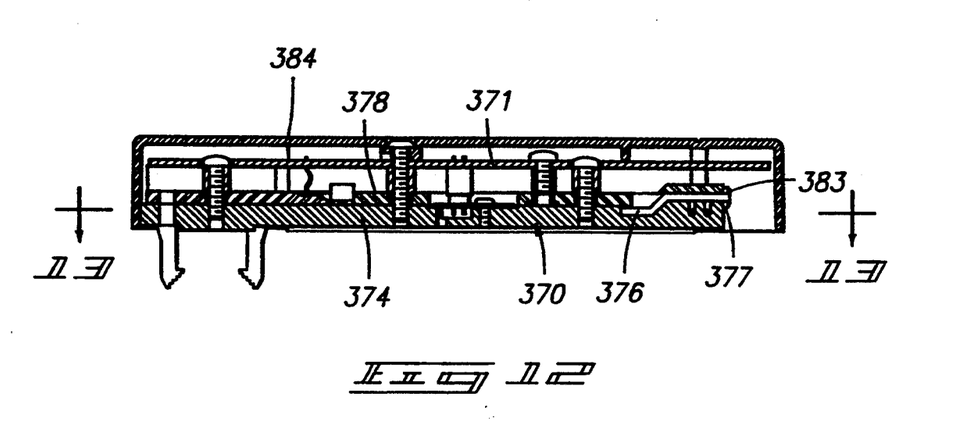
FIG. 12 is a sectional view as seen along line 12—12 in FIG. 10.
Figure 13:
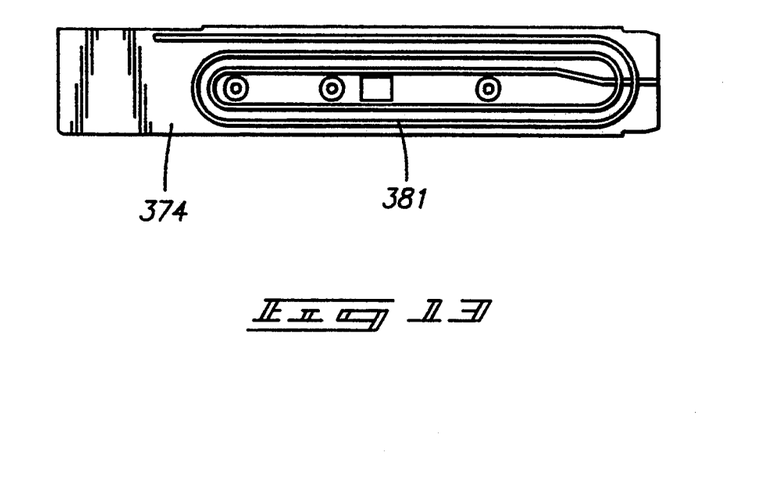
FIG. 13 is a plan view of the bottom casting for the laminated plate in the probe arm, as seen along line 13—13 in FIG. 12.
Figure 14:
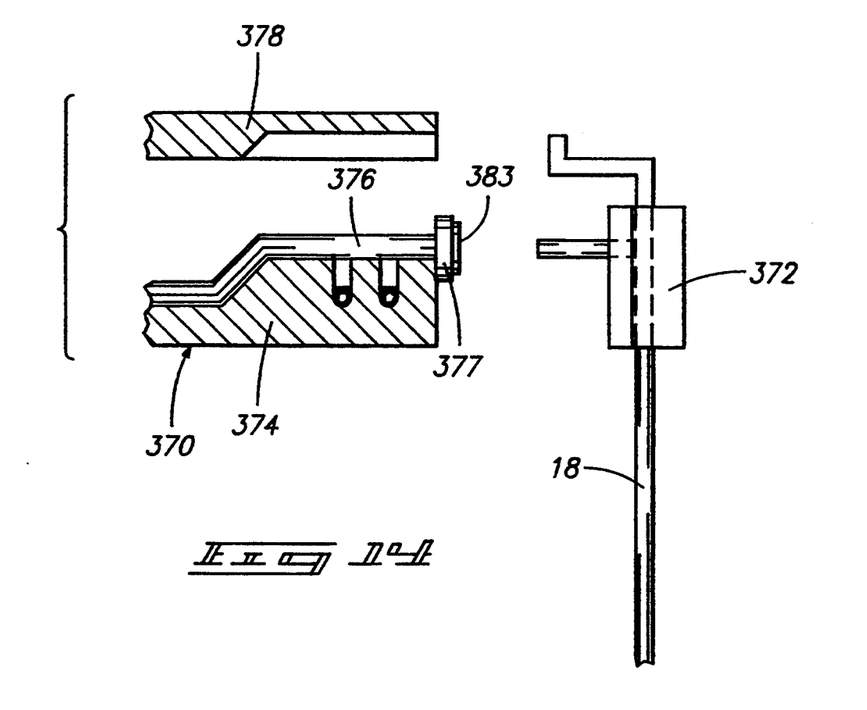
FIG. 14 is an exploded vertical sectional view of the pipette mount.

The vertical limits of movement of shaft 352 relative to the module frame 337 are defined by a protruding flag 355 fixed on guide 350 which passes through lower and upper photo detectors 356, 357, respectively (see FIGS. 7 and 9). Operation of stepper motor 342 is terminated by operation of a microprocessor upon detection of flag 355 being straddled by either of the photo detectors 356 or 357. Stepper motor 342 can accurately position tubular shaft 352 at any elevation between these two extreme elevational limits.

The rotational position of tubular shaft 352 is monitored by a photo detector 358 mounted to circuitboard 341. Photo detector 358 straddles a circular disk 360 clamped to and the upper pulley assembly 353 (see FIGS. 6, 7 and 8). The periphery of disk 360 is radially slotted at 361. Slots 361 are located at angular intervals that properly locate pipette 18 at its required operational positions about the chemistry instrument 24.

To prevent physical damage to probe arm 17 and pipette 18 that might occur due to rotation about the axis A—A beyond its intended range of motion, two motion-limiting pins 362, 363 protrude downwardly from the underside of disk 360 on the pulley assembly 353. The physical stops provided by pins 362 and 363 also prevent the controlling software that governs pivotal motion of probe arm 17 from becoming "lost". They limit the zone of its pivotal motion to the arc including the slots 361 on disk 360.

The rotational paths of pins 362 and 363 abut opposite sides of a fixed bent tab 364 that serves as a stop. Contact of tab 364 by either pin 362 or 363 physically prevents tubular shaft 352 from moving in a complete circle. Such motion would result in damage to probe 18. The limit on rotational movement of tubular shaft 352 further protects the respective lengths of cable 365 and tubing 23 that extend outwardly at the bottom of shaft 352.

Probe arm 17 comprises a rigid laminated plate 370 that supports a parallel printed circuit board 371 located above it. The printed circuit board 371 mounts the circuitry and electrical devices that control and operate the heating functions of plate 370. A conventional electrical connector 373 at one side of printed circuit board 371 is releasably connected to the coupler 367 at the upper end of cable 365 (see FIG. 6).

The laminated plate 370 structurally supports a convoluted liquid path leading to pipette 18. A resistance heater film 381 is laminated to the bottom surface of plate 370 (FIG. 11) for warming liquids traversing the path. Operation of the heater film 381 can be activated to warm liquids along the probe arm 17 to a desired reaction temperature during liquid transport.

Laminated plate 370 is formed from two substantially planar metal castings comprised of aluminum or other metal having good heat distribution qualities. The lower casting 374 carries a flat electrical resistance heating element 375 fixed to it along its bottom surface. Its top surface has a spiralling groove 381 recessed within it to seat an elongated length of flexible tubing 376. Casting 374 and tubing 376 are covered by a complementary metal casting 378 to form a sealed, heat conductive environment for liquid within tubing 376.

Tubing 376 winds along a continuous oval pattern leading from one side edge of plate 374 adjacent the inner end of casting 374 to the center line of casting 374 adjacent its outer end. The outer end of the length of tubing 376 is flared at 383 (FIG. 14) and backed by a rigid washer 377 adhesively secured to the outer end of plate 370. The inner end of tubing 376 is interconnected to the upper end of tubing 23 by a tubular releasible connector.

A pipette mounting bracket 372 is releasably carried at the outer end of heater 370. Bracket 372 supports the bent upper end of a metal pipette 18. An electrically conductive spring clip 382 on bracket 372 provides an electrical path between the pipette 18 and the wiring of circuitboard 371.

The bent upper end of pipette 18 frictionally seats within the open flared end of tubing 376 to form an effective sealed connection between them. Pipette 18 is secured on the laminated plate 370 by mechanically fastening the bracket 372 to its outer end surface in a manner permitting pipette replacement as necessary.

The components of probe arm 17 are protected within the confines of a removable upper cover 384. Temperature sensors can be located about the laminated plate 370 as required to monitor temperature conditions along the fluid path defined within it.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A liquid transfer module for a chemical analyzer, comprising:
   an instrument framework;
   a radially-extended probe arm movably mounted on the framework for effecting transfers of liquids between angularly spaced stations located about the framework, the probe arm having inner and outer ends;
   a vertical, downwardly-extending open pipette mounted to the outer end of the probe arm;
   a vertical tubular shaft fixed to and extending beneath the inner end of the probe arm, the tubular shaft being centered about a fixed vertical axis an the framework;
   bearing means operably connected between the tubular shaft and the framework for supporting the tubular shaft relative to the framework for both elevational and pivotal motion;
   first coaxial drive means operably connected to the tubular shaft for moving it elevationally relative to the framework;
   the first coaxial drive means comprising:
      a first powered rotational element arranged circumferentially about the tubular shaft; and
      a first driving connection between the first powered rotational element and the tubular shaft for imparting rotational motion between them while permitting free relative axial motion in directions parallel to the vertical axis; and second coaxial drive means operably connected to the tubular shaft for moving it angularly relative to the framework;

the second coaxial drive means comprising:

a second powered rotational element arranged coaxially within the tubular shaft at a fixed elevation on, the framework: and a second driving connection between the second powered rotational element and the tubular shaft capable of imparting axial motion to the tubular shaft relative to the second rotational element in directions parallel to the vertical axis while permitting free rotational motion between them.

2. The liquid transfer module of claim 1 wherein the second powered rotational element comprises:

an exteriorly threaded lead screw arranged coaxially within the hollow shaft, the lead screw being rotatably supported at a fixed elevation on the framework;

the second driving connection comprising:

a complementary nut threadably engaged about the lead screw, the nut being physically restrained from rotational motion relative to the framework about the vertical axis; and bearing means operably engaged between the nut and the hollow shaft for imparting conjoint elevational motion to them in directions parallel to the vertical axis in response to rotation of the lead screw.

3. A liquid transfer module for a chemical analyzer, comprising:

an instrument framework having a plurality of liquid transfer stations spaced along a common arc centered about a fixed vertical axis;

a radial probe arm movably mounted on the framework about the axis for effecting transfers of liquids between the spaced stations, the probe arm having inner and outer ends;

a vertical, downwardly-extending open pipette vertically suspended from the outer end of the probe arm;

a vertical tubular shaft fixed to and extending beneath the inner end of the probe arm, the tubular shaft being centered on the framework about the axis;

a bearing assembly connected between the tubular shaft and the framework for supporting the tubular shaft relative to the framework for both elevational movement parallel to the vertical axis and rotational movement about the vertical axis;

first coaxial drive means operably supporting the tubular shaft relative to the framework for selectively positioning the tubular shaft and probe arm elevationally along the vertical axis; and second coaxial drive means operably surrounding the tubular shaft and engaged by the framework for selectively positioning the tubular shaft and probe arm angularly about the vertical axis;

the second coaxial drive means comprising:

an exteriorly threaded lead screw arranged coaxially within the tubular shaft, the lead screw being rotatably supported at a fixed elevation on the framework;

a complementary nut threadably engaged about the lead screw;

a fixed vertical post on the framework engaged by the nut to physically restrain it from rotational motion about the vertical axis; and an axial bearing operably interposed between the nut and the lower end of the tubular shaft for supporting the weight of the tubular shaft and probe arm, the bearing being adapted to impart vertical motion to the tubular shaft in unison with the nut in response to rotation of the lead screw about the vertical axis, the interconnection between the bearing and tubular shaft permitting free rotational movement between the nut and the tubular shaft.

4. The liquid transfer module of claim 3 wherein the first coaxial drive means comprises:

a powered rotational element arranged circumferentially about the tubular shaft; and a key and axial keyway forming a rotational driving connection between the rotational element and the tubular shaft for imparting rotational motion between them about the vertical axis while permitting free relative vertical motion between them.

5. The liquid transfer module of claim 3 wherein the first coaxial drive means comprises:

a rotational element arranged circumferentially about the tubular shaft; and a key and axial keyway forming a rotational driving connection between the rotational element and the tubular shaft for imparting rotational motion between them about the vertical axis while permitting free relative vertical motion between them;

the liquid transfer module further comprising:

a first stepper motor operably connected to the rotational element;

a second stepper motor operably connected to the lead screw;

first sensing means on the framework and the rotational element for monitoring the angular position of the tubular shaft relative to the vertical axis; and second sensing means on the framework and the axial bearing for monitoring the elevational position of the tubular shaft along the vertical axis.

* * * * *